US008871705B2

(12) United States Patent
Seidling et al.

(10) Patent No.: US 8,871,705 B2
(45) Date of Patent: Oct. 28, 2014

(54) LONG-LASTING FRAGRANCE DELIVERY SYSTEM

(75) Inventors: Jeffery Richard Seidling, Appleton, WI (US); Scott W. Wenzel, Neenah, WI (US); Dana Lynn Ramshak, Hortonville, WI (US); Timothy James Van Himbergen, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 13/362,705

(22) Filed: Jan. 31, 2012

(65) Prior Publication Data

US 2013/0196895 A1 Aug. 1, 2013

(51) Int. Cl.
*A61L 9/04* (2006.01)

(52) U.S. Cl.
USPC .......... 512/4

(58) Field of Classification Search
USPC .......... 512/4
See application file for complete search history.

(56) References Cited

U.S. PATENT DOCUMENTS 4,882,220 A 11/1989 Ono et al.
4,898,328 A 2/1990 Fox et al.
4,917,920 A 4/1990 Ono et al.
5,993,972 A 11/1999 Reich et al.
6,063,365 A 5/2000 Shefer et al.
6,291,371 B1 9/2001 Shefer et al.
7,226,607 B2 6/2007 Uchiyama et al.
7,381,417 B2 6/2008 Gamez-Garcia
2005/0020460 A1 1/2005 Goldstein et al.
2005/0176598 A1 8/2005 Bergquist et al.
2005/0218561 A1 10/2005 Watson
2007/0098148 A1 5/2007 Sherman
2009/0232752 A1 9/2009 Carson et al.
2009/0326093 A1 12/2009 Funk et al.
2010/0008957 A1 1/2010 Mundschau et al.
2010/0028270 A1* 2/2010 Nguyen-Kim .......... 424/47
2010/0150851 A1* 6/2010 Zofchak et al. .......... 424/59
2010/0196292 A1* 8/2010 Carson et al. .......... 424/59

FOREIGN PATENT DOCUMENTS

EP 307551 A2 6/1988
EP 1410782 B1 7/2008
GB 1517410 A 12/1976
JP 1272875 A 10/1989

OTHER PUBLICATIONS

International Search Report and Written Opinion for PCT/IB2013/050098 dated May 30, 2013; 12 pages.

* cited by examiner

*Primary Examiner* — Ling Choi
*Assistant Examiner* — Lanee Reuther
(74) *Attorney, Agent, or Firm* — Armstrong Teasdale LLP

(57) ABSTRACT

Long-lasting fragrance delivery systems and uses of the systems to provide fragrance-emitting articles with a long-lasting fragrance are disclosed herein. The long-lasting fragrance delivery systems include an emulsion of silicone-based polyurethane, fragrance, and a carrier.

7 Claims, No Drawings

LONG-LASTING FRAGRANCE DELIVERY SYSTEM

BACKGROUND OF THE DISCLOSURE

The present disclosure relates generally to long-lasting fragrance delivery systems and uses of the systems to provide articles with a long-lasting fragrance. More particularly, the articles include at least one substrate having disposed thereon at least one film layer including a fragrance.

Consumers enjoy it when a substrate carries with it the smell of a fragrance. Examples are abundant and range from scented letters to washed textile fabrics and so forth. To provide the pleasing smell of freshly washed fabric or to perfume a substrate, the substrate is commonly treated, typically by spraying, coating or dipping, with a perfume or fragrance. The effects of imparted fragrance on substrates, however, are often short-lived. Particularly, the fragrance is lost over time to the environment.

Further, when applied to substrates, particularly, substrates that will contact a user's skin, the types and amounts of oils and other components of the fragrances that can be used are limited. Skin sensitivity to particular oils and scents can limit available fragrances, as well as the amounts of oils and other components used in the fragrances. Additionally, particular fragrances and their components can damage the substrates themselves, such as by staining and degrading the substrate material.

Conventionally, solutions for the above problems have included incorporating fragrances into substrates through the use of encapsulates. While the encapsulates may protect the consumer's skin from sensitivities to the fragrances, and further, may protect the substrates themselves from the destructive effects of the fragrances, encapsulates are costly and difficult to apply.

Other chemistries that have been used to apply the fragrances to the substrates have met with similar disadvantages. For example, often times the machinery that converts substrates into finished products runs very rapidly, limiting both the drying time of any applied chemistry as well as where the chemistry can be applied in the processing line.

As such, there is a significant need for a fragrance delivery system that can easily be applied to substrates that will provide long-lasting fragrance to the substrate. The fragrance is desirably applied to the surface of nonwoven, elastomeric, and/or tissue paper substrates such to provide slow release over an extended period. Additionally, it would be advantageous if the fragrance could be applied such to not damage the substrate, and in some embodiments, to not induce a hypersensitive response by the user of the substrate.

BRIEF DESCRIPTION OF THE DISCLOSURE

It has been found that a fragrance delivery system including an emulsion formulation can be produced and applied to substrates and articles for providing a long-lasting fragrance. The fragrance delivery system can be applied without the use of high temperature drying, which can prevent shortening of the fragrance's effectiveness and can further reduce production costs. Particularly, these fragrance delivery systems include components that can provide long-lasting fragrance to a substrate without damaging the article or irritating a user's skin. In one embodiment, particularly preferred substrates for use with the fragrance delivery system include nonwoven substrates and elastomeric substrates such as used in patches and absorbent articles. In another embodiment, the fragrance delivery system can be applied to tissue paper to provide a fragrance to the paper. Generally, the fragrance delivery system can include an emulsion of a silicone-based polyurethane, a fragrance, and a carrier.

Accordingly, the present disclosure is directed to a fragrance delivery system comprising an emulsion comprising a silicone-based polyurethane having a polymeric backbone comprising at least one lipophilic moiety and at least one hydrophilic moiety, a fragrance, and a carrier.

The present disclosure is further directed to a fragrance-emitting article comprising a substrate comprising a film layer. The film layer comprises a silicone-based polyurethane having a polymeric backbone comprising at least one lipophilic moiety and at least one hydrophilic moiety and a fragrance.

The present disclosure is further directed to a method of manufacturing a fragrance-emitting article. The method comprises: contacting a fragrance with a carrier to solubilize the fragrance; preparing an emulsion by blending the fragrance with a silicone-based polyurethane having a polymeric backbone comprising at least one lipophilic moiety and at least one hydrophilic moiety; applying the emulsion to a substrate; and drying the emulsion to form a film layer on at least one surface of the substrate.

Other objects and features will be in part apparent and in part pointed out hereinafter.

DETAILED DESCRIPTION OF THE DISCLOSURE

The present disclosure is directed to a fragrance delivery system for providing an article with a long-lasting fragrance. The fragrance delivery system includes an emulsion that can be applied to one or more substrates of an article in the form of a film layer for providing long-lasting fragrance to the article. The film layer further provides improved protection to the substrates and articles from damage due to the fragrance and to users of the articles against sensitivities of their skin to the fragrances and components used therein. Generally, the articles can include nonwoven, elastomeric, cardboard or tissue paper substrates.

Additionally, the present disclosure is directed to fragrance-emitting articles including one or more substrates with a long-lasting fragrance. Particularly, the fragrance-emitting articles have at least one substrate in which the fragrance delivery system has been applied thereon to form a film layer including a fragrance.

Fragrance Delivery System

The fragrance delivery system of the present disclosure generally includes an emulsion that can be applied to one or more substrates and dried to form a film layer upon the substrate. The formed film layers are capable of providing an article with a long-lasting fragrance. As used herein "long-lasting fragrance" refers to a fragrance that is effective in providing a scent to a substrate upon exposure of the fragrance in the film layer to a triggering event (e.g., exposure to air, change in temperature, change in pH, friction, etc.) that can be perceived by a user for a period of at least 30 minutes, including at least 1 hour, including at least 2 hours, including at least 3 hours, and including at least 4 hours or longer. For example, in one embodiment, the substrate is a nonwoven patch to be attached to the undergarment of a user. As the patch is worn by the user, the substrate is exposed to body heat and friction, triggering the release of the fragrance. The fragrance is emitted upon these triggering events for a period of at least 4 hours or longer, thereby protecting the user from undesirable odor (e.g., feminine odor caused by perspiration, hormones, and/or incontinence).

Generally, the emulsions for use in the fragrance delivery systems of the present disclosure include a silicone-based polyurethane having a polymeric backbone including at least one lipophilic moiety and at least one hydrophilic moiety, a fragrance, and a carrier. It has been surprisingly found that the silicone-based polyurethane can be combined with the fragrance and carrier to form an emulsion that can be dried into a film layer that entraps the fragrance such to slow release of the fragrance to the surrounding environment. This allows for a long-lasting fragrance-emitting article to be provided. Further, it has been found that the emulsion of silicone-based polyurethane, fragrance and carrier dries quickly without the use of expensive drying equipment that can flash off the fragrance and shorten the life thereof. More particularly, in one embodiment, the carrier and/or the aqueous phase of the emulsion can be evaporated within seconds of the emulsion being applied to the substrate, including evaporated after 30 seconds of the emulsion being applied to the substrate, including evaporated after 20 seconds of the emulsion being applied to the substrate, including evaporated after 15 seconds of the emulsion being applied to the substrate, including evaporated after 10 seconds of the emulsion being applied to the substrate, and including evaporated after 5 seconds or less of the emulsion being applied to the substrate.

The silicone-based polyurethane used in the emulsion of the fragrance delivery system includes a polymeric backbone having at least one lipophilic moiety and at least one hydrophilic moiety. In one embodiment, the hydrophilic moiety is a dimethicone polyether. For example, one particularly suitable hydrophilic moiety includes the crosslinked compound, bis-(polyethylene glycol)$_x$ dimethicone, also referred to as Bis-PEG-X Dimethicone, wherein x ranges from 8 to 20, including a range of from 10 to 17, and including from 12 to 16. In one embodiment, the hydrophilic moiety is Bis-PEG-15 Dimethicone.

One suitable lipophilic moiety for use in the backbone of the silicone-based polyurethane includes isophorone diisocyanate (IPDI).

One particularly suitable silicone-based polyurethane is prepared to include crosslinked Bis-PEG-X Dimethicone, wherein x ranges from 8 to 20, and isophorone diisocyanate. One exemplary silicone-based polyurethane is Bis-PEG-15 Dimethicone/IPDI copolymer (CAS #190793-18-1), commercially available as Polyderm PPI SIWS, from Alzo International Corporation (Sayreville, N.J.).

In addition to the silicone-based polyurethane, the emulsion includes a lipophilic fragrance. Any lipophilic fragrance known in the art is suitable for use in the emulsion described herein. Exemplary suitable lipophilic fragrances are commercially available from Symrise AG (Holzminden, Germany), Firmenich (St. Louis, Mo.), and Bell Flavors and Fragrance (Northbrook, Ill.). In some embodiments, the fragrances include essential oils such as lavender, orange, peppermint, and the like.

In one embodiment, in addition to the fragrance in the emulsion, the fragrance delivery system may optionally include additional fragrance that has been encapsulated. Accordingly, once the fragrance of the emulsion is used, the encapsulated fragrance can provide additional fragrance, allowing for an even further extended release of fragrance.

Any encapsulation materials known in the art are suitable for encapsulating the additional fragrance. Without being limiting, suitable encapsulation materials include cellulose-based polymeric materials (e.g., ethyl cellulose), carbohydrate-based materials (e.g., cationic starches and sugars), polyglycolic acid, polylactic acid, and lactic acid-based aliphatic polyesters, and materials derived therefrom (e.g., dextrins and cyclodextrins).

Typically, the emulsion includes the silicone-based polyurethane and fragrance in a weight ratio of silicone-based polyurethane to fragrance of from about 3:1 to about 1:3, including from about 2:1 to about 1:2, and including about 1:1. The amounts of silicone-based polyurethane and fragrance should be adjusted such to effectively dissolve in the carrier and dry to form a film layer entrapping the fragrance to allow for a slow release. Weight ratios having higher amounts of silicone-based polyurethane than the above ranges may detract from fragrance intensity, while lower amounts of silicone-based polyurethane may not be sufficient to form a film layer capable of entrapping the fragrance.

The emulsion further includes at least one carrier. Suitable carriers include volatile carriers including, but not limited to, water, methanol, ethanol, isopropanol, butanol, and combinations thereof, and suitably include ethanol and isopropanol. The selection of carrier will vary depending on the silicone-based polyurethane and fragrance used and the substrate for application of the resulting fragrance delivery system and must be chosen so as to ensure that the silicone-based polyurethane and fragrance are sufficiently solubilized in the carrier such to allow application of the fragrance delivery system onto the substrate without causing separation of the emulsion in the system.

It has been found that when combined, the silicone-based polyurethane and fragrance readily dissolve in the carrier, forming an emulsion. The carrier quickly evaporates and the emulsion forms a protected film layer of fragrance, which is released slowly over time upon application to a substrate and exposure to one or more triggering events (e.g., exposure to air, change in temperature, change in pH, friction, etc.). The fragrance is detectable for a longer duration of time as compared to a similar amount of fragrance without the silicone-based polyurethane. Particularly, the fragrance is detectable upon exposure to a triggering event for a period of at least 30 minutes, including at least 1 hour, including at least 2 hours, including at least 3 hours, and including at least 4 hours or longer.

The amount of carrier in the emulsion will typically depend on the other components and amounts of components in the emulsion. The emulsion for use in the fragrance delivery system of the present disclosure may include both concentrated and diluted forms.

Typically, the carrier will be present in the emulsion in an amount of from about 4% (by weight formulation) to about 94% (by weight formulation), including from about 10% (by weight formulation) to about 70% (by weight formulation), and even more suitably, from about 20% (by weight formulation) to about 50% (by weight formulation).

In one embodiment, at least a portion of the emulsion can optionally be encapsulated prior to being applied to a substrate as described below to provide a further extended release of the fragrance. By way of example, a portion of the emulsion is encapsulated and applied with the remaining emulsion in a mixture to a substrate. As the fragrance is used from the emulsion directly contacted with the substrate, the microcapsules of additional emulsion are broken to release additional fragrance to the substrate, allowing for an even longer lasting fragrance release from the substrate.

When the fragrance delivery system includes emulsion in encapsulation form, at least about 0.1% by weight total emulsion in the fragrance delivery system of the present disclosure is encapsulated, including from about 0.1% by weight to about 50% by weight total emulsion, including from about 0.5% by weight to about 25% by weight total emulsion, and including from about 1% by weight to about 10% by weight total emulsion is encapsulated.

Any encapsulation materials known in the art are suitable herein. Without being limiting, suitable encapsulation materials include cellulose-based polymeric materials (e.g., ethyl cellulose), carbohydrate-based materials (e.g., cationic starches and sugars), polyglycolic acid, polylactic acid, and lactic acid-based aliphatic polyesters, and materials derived therefrom (e.g., dextrins and cyclodextrins).

The fragrance delivery system may include one or more optional components to provide additional benefits to the fragrance-emitting articles to which the systems are applied. For example, when used with personal care products, such as diapers, feminine care products, absorbent pads and the like, the fragrance delivery system may include skin benefiting agents, for example: emollients, skin barrier enhancers, humectants, deodorants, moisture absorbents, and combinations thereof.

Generally, emollients lubricate, sooth, and soften the skin surface. Exemplary emollients include oily or waxy ingredients such as esters, ethers, fatty alcohols, hydrocarbons, silicones, and the like, and combinations thereof.

Skin barrier enhancers, also referred to as occlusive materials, increase the water content of the skin by blocking water evaporation. These materials generally include lipids which tend to remain on the skin surface or hydrocarbons such as petrolatum and wax.

Humectants are hydroscopic agents that are widely used as moisturizers. Their function is to prevent the loss of moisture from the skin and to attract moisture from the environment. Common humectants include, for example, glycerin, butylene glycol, betaine, sodium hyaluronate, and the like, and combinations thereof.

Still other optional components that may be desirable for use with the fragrance delivery systems of the present disclosure include those cosmetic and pharmaceutical ingredients commonly used in the skin care industry. Examples include abrasives, absorbents, aesthetic components (pigments, colorings/colorants), anti-caking agents, antifoaming agents, antimicrobial agents, antioxidants, binders, biological additives, buffering agents, bulking agents, chelating agents, chemical additives, preservatives, pH adjusters, skin-conditioning agents, skin soothing and/or healing agents (e.g., panthenol and derivatives thereof), aloe vera, pantothenic acid and derivatives thereof, allantoin, bisabolol, dipotassium glycyrrhizinate, skin treating agents, sunscreens, thickeners, and vitamins, and combinations thereof. Examples of these and other agents are disclosed in The CTFA Cosmetic Ingredient Handbook, 12th Ed. (2007), which is hereby incorporated by reference to the extent that it is consistent herewith.

The amounts of the optional components will depend on the fragrance-emitting article to be prepared with the fragrance delivery system and the amounts of the other components in the fragrance delivery system.

Film Layer(s) Prepared from the Fragrance Delivery Systems

Surprisingly, it has been found that the emulsions of the fragrance delivery systems described above may be dried to form one or more film layers on the surface of one or more substrates described herein to form a fragrance-emitting article. The film layer entraps the fragrance therein, providing for a slow release, and thus a long-lasting, fragrance. More particularly, upon drying, the carrier evaporates off and the silicone-based polyurethane of the emulsion forms a film network in which the fragrance is entrapped. The entrapped fragrance is still allowed to diffuse from the film layer on the substrate, but at a much slower rate, thus allowing for a long lasting fragrance to be perceived by the user.

Furthermore, the film layer further protects the substrates from oils and other components in the fragrance. For instance, in some cases, the components of the fragrance for use in the fragrance delivery systems may discolor or damage the fibers of the substrates. By entrapping the fragrance within the film layer, the substrate is protected from such damage. Similarly, the skin of the user of fragrance-emitting articles including substrates having the film layer applied thereon is also protected from direct contact with the fragrance and its components. This may protect users from skin irritation and allergic reactions commonly resulting from contact with the fragrance.

In one embodiment, the film layer may be a single layer. In another embodiment, multiple emulsions may be prepared and subsequently dried such to provide multiple film layers layered one on top of the other, such as including two film layers, including three film layers, including four film layers, and including five film layers or even more.

The thickness of the film layer(s) will depend on the amount of emulsion deposited onto one or more of the substrates described herein. Depending on the amount of fragrance intensity desired and the length of time the fragrance is needed, one skilled in the art could readily determine the amount of emulsion to deposit.

Typically, it is suitable to apply the emulsion onto the substrate in an amount of from about 0.10% by weight add-on to about 800% by weight add-on, including from about 0.30% by weight add-on to about 400% by weight add-on, including from about 0.45% by weight add-on to about 160% by weight add-on, and including from about 4% by weight add-on to about 20% by weight add-on. In one desirable embodiment, the substrate is a nonwoven patch having a dry weight of about 0.063 grams. Suitably, the emulsion of the fragrance delivery system of the present disclosure can be applied to the nonwoven patch in an amount of from about 0.1 mg to about 50 g to form a single film layer. More particularly, from about 0.2 mg to about 25 g of emulsion is applied to the nonwoven patch, and even more particularly, from about 0.3 mg to about 1.0 g of emulsion is applied to the nonwoven patch and dried to form a single film layer.

Representative Substrates/Fragrance-Emitting Articles for Use with the Fragrance Delivery Systems In one embodiment, the substrate is a nonwoven substrate. When a nonwoven substrate is used with the emulsions of the fragrance delivery system of the present disclosure, commercially available thermoplastic polymeric materials can be advantageously employed in making the fibers or filaments from which the substrate is formed. As used herein, the term "polymer" shall include, but is not limited to, homopolymer, copolymers, such as for example, block, graft, random and alternating copolymers, terpolymers, etc., and blends and modifications thereof. Moreover, unless otherwise specifically limited, the term "polymer" shall include all possible geometric configurations of the material, including, without limitation, isotactic, syndiotactic, random and atactic symmetries. As used herein, the terms "thermoplastic polymer" or "thermoplastic polymer material" refer to a long-chain polymer that softens when exposed to heat and returns to the solid state when cooled to ambient temperature. Exemplary thermoplastic materials include, without limitation, polyvinyl chlorides, polyesters, polyamides, polyfluorocarbons, polyolefins (e.g., polypropylene (PP), polyethylene (PE), polyethylene terephthalate (PET, PETE)), polyurethanes, polystyrenes, polyvinyl alcohols, caprolactams, and copolymers thereof.

Alternatively, or in addition to the polymeric materials above, the nonwoven substrates can be prepared from cellulosic fibers. Numerous cellulosic fibers, such as, for example, wood pulp fibers or staple fibers can be used in the nonwoven substrates. Suitable commercially available cellulosic fibers for use in the nonwoven substrates can include, for example, NF 405, which is a chemically treated bleached southern softwood Kraft pulp, available from Weyerhaeuser Co. of Federal Way (Wash.); NB 416, which is a bleached southern softwood Kraft pulp, available from Weyerhaeuser Co.; CR-0056, which is a fully debonded softwood pulp, available from Bowater, Inc. (Greenville, S.C.); Golden Isles 4822 debonded softwood pulp, available from Koch Cellulose (Brunswick, Ga.); and SULPHATATE HJ, which is a chemically modified hardwood pulp, available from Rayonier, Inc. (Jesup, Ga.).

Nonwoven substrates can be formed by a variety of known forming processes, including airlaying, meltblowing, spunbonding, or bonded carded web formation processes. "Airlaid" refers to a porous web formed by dispersing fibers in a moving air stream prior to collecting the fibers on a forming surface. The collected fibers are then typically bonded to one another using, for example, hot air or a spray adhesive.

The fibrous nonwoven substrate material may also comprise meltblown materials. "Meltblown" refers to fibers formed by extruding a molten thermoplastic material through a plurality of fine, usually circular, die capillaries as molten threads or filaments into converging high velocity gas (e.g., air) streams, generally heated, which attenuate the filaments of molten thermoplastic material to reduce their diameters. Thereafter, the meltblown fibers are carried by the high velocity gas stream and are deposited on a collecting surface or support to form a web of randomly dispersed meltblown fibers. Meltblowing processes can be used to make fibers of various dimensions, including macrofibers (with average diameters from about 40 to about 100 microns), textile-type fibers (with average diameters between about 10 and 40 microns), and microfibers (with average diameters less than about 10 microns). Meltblowing processes are particularly suited to making microfibers, including ultra-fine microfibers (with an average diameter of about 3 microns or less). Meltblown fibers may be continuous or discontinuous and are generally self bonding when deposited onto a collecting surface.

"Spunbonded fibers" or "spunlaced fibers" refers to small diameter fibers which are formed by extruding molten thermoplastic material as filaments from a plurality of fine, usually circular capillaries of a spinneret with the diameter of the extruded filaments then being rapidly reduced to fibers. Spunbond fibers are generally continuous and have diameters generally greater than about 7 microns, more particularly, between about 10 and about 20 microns.

"Bonded-carded web" refers to a web made from staple fibers sent through a combing or carding unit, which separates or breaks apart and aligns the fibers to form a nonwoven web. For example, the web may be a powder bonded carded web, an infrared bonded carded web, or a through-air bonded carded web.

In one particularly suitable embodiment, the substrate is a spunbonded substrate made from 50:50 PET and rayon.

In another embodiment, the substrate is an elastomeric substrate. Elastomeric substrates are particularly useful when the substrate is to be used in a laminated article such as a glove or sock, as it is oftentimes desirable for the glove or sock to be able to stretch to provide for easier glove/sock donning. The elastomeric substrate may be formed from a natural or a synthetic latex as well as a dissolved or hot melt extrusion of an elastomeric polymer, such as a thermoplastic elastomeric polyolefin polymer. For instance, the elastomeric substrate may be formed of a natural or synthetic rubber, a nitrile rubber, a nitrile butadiene rubber, a polyisoprene, a polychloroprene, a polyurethane, a neoprene, a homopolymer of a conjugated diene, a copolymer of a least two conjugated dienes, a copolymer of at least one conjugated diene and at least one vinyl monomer, styrene block copolymers, or any other suitable combinations thereof. Examples of suitable synthetic rubbers can also include acrylic diene block copolymers, acrylic rubber, butyl rubber, EPDM rubber, polybutadiene, chlorosulfonated polyethylene rubber, and fluororubber.

The elastomeric substrates can be formed by mixing the components together, heating and then extruding the components into a mono-layer or multi-layer substrate using any one of a variety of elastomeric-producing processes known to those of ordinary skill in the elastomeric processing art. Such elastomeric-producing processes include, for example, cast embossed, chill and flat cast, and blown film processes.

As noted above, these substrates can be used alone or can be combined to form articles having long-lasting fragrance, referred to herein as fragrance-emitting articles.

The substrates including the film layer may be configured to be used in various fragrance-emitting articles, non-limiting examples of which may include patches, absorbent articles, cardboard packaging, clothing, and the like. For example, in a particularly suitable embodiment, the substrate is a patch to adhere to a user's undergarment or other personal article of clothing to provide protection against bodily odor. The patch could alternatively act as an air freshener, such as an air freshener for a car, room, closet, drawer, and the like. In another embodiment, the substrates include the outer layers and/or inner bodyfacing layers of personal care products including diapers, absorbent pads, feminine care products, training pants, and swimwear. Articles of clothing such as in the form of a glove, mitten, sock, sleeve, or other article designed to be fitted to a part of the user's body could also be made from the substrates used herein.

Alternatively, the emulsion may be applied to form a film layer on a tissue paper, paper towel, and/or napkin. As used herein, the terms "tissue paper web," "paper web," "web," and "paper sheet" all refer to sheets of paper made by a process comprising the steps of forming an aqueous papermaking furnish, depositing this furnish on a foraminous surface, such as a Fourdrinier wire, and removing the water from the furnish as by gravity or vacuum-assisted drainage, with or without pressing, and by evaporation. Tissue paper may include facial tissue, toilet tissue, and the like.

Methods of Manufacturing Fragrance-Emitting Articles

As described above, fragrance-emitting articles of the present disclosure are generally prepared by depositing the fragrance delivery system onto an article as described above. More particularly, the emulsion of the fragrance delivery system as described herein is prepared and applied to a substrate, wherein the emulsion, and particularly the carrier and/or aqueous phase in the emulsion, is dried, forming a film layer on the surface of the substrate. The film layer provides a slow release of fragrance from the article.

The emulsion is prepared by contacting the fragrance with a carrier to solubilize the fragrance. The fragrance can be partly or completely solubilized in the carrier, however, in one embodiment, the fragrance is desirably completely (i.e., 100% by weight) solubilized in the carrier.

Once contacted and solubilized within the carrier, the fragrance is then blended with the silicone-based polyurethane. The blending conditions will vary depending on the silicone-based polyurethane and fragrance used as well as the amounts of each. The silicone-based polyurethane and fragrance are typically blended, however, under ambient temperatures until a homogenous solubilized mixture of the silicone-based polyurethane and fragrance is formed.

The silicone-based polyurethane and fragrance are blended in a weight ratio of silicone-based polyurethane to fragrance of from about 3:1 to about 1:3, including from about 2:1 to about 1:2, and including about 1:1.

The resulting emulsion is then applied to a surface of a substrate. As described herein as application of the emulsion, it should be understood that the entire fragrance delivery system is applied to the substrate, including any optional components described herein in addition to the emulsion of silicone-based polyurethane, fragrance, and carrier.

The emulsion may be applied to the substrate using any means known in the emulsion application art, including, for example, coating, spraying, dripping, dipping, and combinations thereof. In one particularly desirable embodiment, the emulsion is applied to the substrate using slot die coating. Using the slot die coating process has been found to provide good add-on control.

The emulsion can be applied to one or more surfaces of the substrate, including an outer surface, an inner surface, ends or edges of the substrate, and combinations thereof. Furthermore, the emulsion can be applied to one or more substrates of an article. For example, in one embodiment, the fragrance-emitting article is an absorbent article and the emulsion can be applied to one or more of the impermeable outer layer, the permeable bodyfacing inner layer, or the absorbent core located in between the outer and inner layers.

Once applied to the substrate, the emulsion is dried to form the film layer. In one particularly suitable embodiment, the emulsion is dried by evaporation; that is, the carrier and/or the aqueous phase is evaporated, to form the film layer. Advantageously, evaporation avoids flashing off the fragrance from the emulsion, providing desired fragrance intensity in the resulting fragrance-emitting article, and further, reduces processing costs of the article as high cost dryers can be avoided.

The emulsion can be dried within seconds of being applied to the substrate, including dried after 30 seconds of being applied to the substrate, including dried after 20 seconds of being applied to the substrate, including dried after 15 seconds of being applied to the substrate, including dried after 10 seconds of being applied to the substrate, and including dried after 5 seconds or less of being applied to the substrate.

Other suitable methods of drying the emulsion include air drying using an air dryer or impingement dryer as known in the art.

Having described the disclosure in detail, it will be apparent that modifications and variations are possible without departing from the scope of the disclosure defined in the appended claims.

EXAMPLE

The following non-limiting example is provided to further illustrate the present disclosure.

Example 1

In this Example, various fragrance-emitting emulsions were applied to patch substrates and the ability of the emulsions to provide long-lasting fragrance was evaluated.

The emulsions shown in Table 1 below were prepared using methods described herein and applied to 32-mm patches. The patches were made of spunbonded 50% rayon/50% PET fibers.

TABLE 1

| Ingredient | A2 | B2 | C2 | D2 | E2 | F2 | G2 | H2 | I2 | Control |
|---|---|---|---|---|---|---|---|---|---|---|
| | Grams | | | | | | | | | |
| Bis-PEG-15 Dimethicone/IPDI Copolymer (Polyderm PPI SIWS available from ALZO International Corporation) | 1.5 | 3 | 4.5 | | | | | | | |
| PEG-40 Hydrogenated Castor Oil/IPDI Copolymer (Polyderm PPI CO40 available from ALZO International Corporation) | | | | 1.5 | 3 | 4.5 | | | | |
| Acrylates/Octylacrylamide Copolymer (Dermacryl 79 available from Akzo Nobel) | | | | | | | 1.5 | 3 | 4.5 | |
| Fragrance (Symrise) | 1.5 | 1.5 | 1.5 | 1.5 | 1.5 | 1.5 | 1.5 | 1.5 | 1.5 | 1.5 |
| SD Alcohol 40B 190 Proof (available from Grain Processing Corporation) | 47 | 45.5 | 44 | 47 | 45.5 | 44 | 47 | 45.5 | 44 | 48.5 |
| Total (grams) | 50 | 50 | 50 | 50 | 50 | 50 | 50 | 50 | 50 | 50 |
| Ratio Film Former: Fragrance | 1:1 | 2:1 | 3:1 | 1:1 | 2:1 | 3:1 | 1:1 | 2:1 | 3:1 | N/A |

The patches were first placed on a plastic weigh boat with an analytical balance scale, tared to zero, to get a neat patch weight. The patch was removed from the analytical balance, placed on a clean plastic weigh boat and sprayed with approximately 2-3 sprays. The patch was again placed on the analytical balance scale and the process above was repeated until approximately 0.1 grams of add-on emulsion was achieved. The sample emulsions were then placed in clean, labeled, 37-mm metal weight boats to dry. The above process was then repeated for 3-mg and 6-mg add-on emulsion samples. For the 6-mg add-on samples, the above process was followed except approximately 0.2 grams (i.e., 4-6 sprays) were added. The emulsion samples were allowed to dry at room temperature for approximately 4 hours. The patch samples and add-on weights are shown in Table 2 below.

TABLE 2

| | A2(3) | B2(3) | C2(3) | D2(3) | E2(3) | F2(3) | G2(3) | H2(3) | I2(3) | Control | |
|---|---|---|---|---|---|---|---|---|---|---|---|
| Patch Weight (grams) | 0.0698 | 0.0678 | 0.0723 | 0.0718 | 0.0695 | 0.0700 | 0.0744 | 0.0700 | 0.0723 | 0.0734 | Approx 3-mg add-on |
| Weight after Spray (grams) | 0.1624 | 0.1590 | 0.1654 | 0.1658 | 0.1635 | 0.1965 | 0.1764 | 0.1726 | 0.1853 | 0.1612 | |
| Add-on weight (grams) | 0.0926 | 0.0912 | 0.0931 | 0.0940 | 0.0940 | 0.1265 | 0.1020 | 0.1026 | 0.1130 | 0.0878 | |
| | A2(6) | B2(6) | C2(6) | D2(6) | E2(6) | F2(6) | G2(6) | H2(6) | I2(6) | Control | |
| Patch Weight (grams) | 0.0703 | 0.0698 | 0.0714 | 0.0729 | 0.0674 | 0.0678 | 0.0695 | 0.0725 | 0.0702 | 0.0697 | Approx 6-mg add-on |
| Weight after Spray (grams) | 0.2646 | 0.2761 | 0.2664 | 0.2667 | 0.2769 | 0.2906 | 0.2767 | 0.2619 | 0.2963 | 0.2707 | |
| Add-on weight (grams) | 0.1943 | 0.2063 | 0.1950 | 0.1938 | 0.2095 | 0.2228 | 0.2072 | 0.1894 | 0.2261 | 0.2010 | |

Eight or nine participants were then chosen at random and instructed to smell an array of triad groups and rank them 1-3 (1 having the highest fragrance intensity and 3 having the lowest fragrance intensity). The first group of participants compared how varying film former amount affects fragrance longevity. The results are shown in Table 3 below.

TABLE 3

| 3 Mg Wet Add-on | | | | | | | | | |
|---|---|---|---|---|---|---|---|---|---|
| | Film Former | | | | | | | | |
| | PPI SI WS | | | PPI CO40 % | | | Dermacryl 79 | | |
| | 3% | 6% | 9% | 3% | 6% | 9% | 3% | 6% | 9% |
| | Code | | | | | | | | |
| | A2(3) | B2(3) | C2(3) | D2(3) | E2(3) | F2(3) | G2(3) | H2(3) | I2(3) |
| | 1 | 2 | 2 | 2 | 2 | 1 | 1 | 2 | 2 |
| | 1 | 3 | 2 | 1 | 2 | 3 | 2 | 3 | 1 |
| | 1 | 2 | 3 | 1 | 2 | 3 | 1 | 3 | 2 |
| | 1 | 2 | 3 | 1 | 2 | 3 | 1 | 2 | 3 |
| | 1 | 2 | 2 | 3 | 1 | 2 | 1 | 2 | 3 |
| | 1 | 2 | 3 | 2 | 1 | 3 | 1 | 2 | 3 |
| | 1 | 2 | 3 | 1 | 3 | 2 | 1 | 2 | 3 |
| | 1 | 1 | 3 | 1 | 2 | 1 | 1 | 2 | 2 |
| Total | 8 | 16 | 21 | 12 | 15 | 18 | 9 | 18 | 19 |
| Average | 1.00 | 2.00 | 2.63 | 1.50 | 1.88 | 2.25 | 1.13 | 2.25 | 2.38 |

The same participants were then instructed to smell another array of triad groups and rank them 1-3 for fragrance intensity. This second group of participants compared how varying film former type affects fragrance longevity. The results are shown in Table 4 below.

TABLE 4

| 3 Mg Wet Add-on | | | | | | | | | |
|---|---|---|---|---|---|---|---|---|---|
| | % | | | | | | | | |
| | 3% | | | 6% Film Former | | | 9% | | |
| | PPI SIWS | PPI CO40 | Derm 79 | PPI SIWS | PPI CO40 Code | Derm 79 | PPI SIWS | PPI CO40 | Derm 79 |
| | A2(3) | D2(3) | G2(3) | B2(3) | E2(3) | H2(3) | C2(3) | F2(3) | I2(3) |
| | 1 | 2 | 2 | 1 | 2 | 2 | 2 | 1 | 2 |
| | 1 | 3 | 2 | 1 | 2 | 3 | 2 | 1 | 3 |
| | 1 | 2 | 3 | 2 | 1 | 3 | 1 | 3 | 2 |
| | 1 | 2 | 3 | 1 | 2 | 3 | 1 | 2 | 3 |
| | 2 | 3 | 1 | 2 | 1 | 2 | 1 | 2 | 2 |
| | 3 | 1 | 2 | 3 | 1 | 2 | 2 | 1 | 3 |
| | 1 | 3 | 2 | 3 | 2 | 1 | 2 | 3 | 1 |
| | 1 | 3 | 2 | 1 | 1 | 1 | 2 | 1 | 2 |
| | 1 | 2 | 2 | 2 | 1 | 1 | 2 | 1 | 2 |
| Total | 12 | 21 | 19 | 16 | 13 | 18 | 15 | 15 | 20 |
| Average | 1.33 | 2.33 | 2.11 | 1.78 | 1.44 | 2.00 | 1.67 | 1.67 | 2.22 |

After a brief rest period (approximately 5 minutes), the participants repeated the same triad comparisons above for the 6-mg add-on samples. The results are shown in Tables 5 and 6 below.

TABLE 5

| 6 Mg Wet Add-on | | | | | | | | | |
|---|---|---|---|---|---|---|---|---|---|
| | Film Former | | | | | | | | |
| | PPI SI WS | | | PPI CO40 % | | | Dermacryl 79 | | |
| | 3% | 6% | 9% | 3% | 6% Code | 9% | 3% | 6% | 9% |
| | A2(6) | B2(6) | C2(6) | D2(6) | E2(6) | F2(6) | G2(6) | H2(6) | I2(6) |
| | 2 | 1 | 2 | 3 | 2 | 1 | 1 | 2 | 3 |
| | 1 | 2 | 3 | 2 | 1 | 3 | 1 | 2 | 3 |

TABLE 5-continued

| 6 Mg Wet Add-on | | | | | | | | | |
|---|---|---|---|---|---|---|---|---|---|
| | Film Former | | | | | | | | |
| | PPI SI WS | | | PPI CO40 % | | | Dermacryl 79 | | |
| | 3% | 6% | 9% | 3% | 6% | 9% | 3% | 6% | 9% |
| | Code | | | | | | | | |
| | A2(6) | B2(6) | C2(6) | D2(6) | E2(6) | F2(6) | G2(6) | H2(6) | I2(6) |
| | 1 | 2 | 3 | 2 | 3 | 1 | 1 | 3 | 2 |
| | 1 | 2 | 3 | 1 | 3 | 2 | 1 | 2 | 3 |
| | 1 | 2 | 3 | 3 | 1 | 2 | 1 | 2 | 3 |
| | 2 | 1 | 3 | 3 | 1 | 2 | 1 | 2 | 3 |
| | 1 | 3 | 2 | 3 | 2 | 1 | 1 | 2 | 3 |
| | 1 | 2 | 2 | 1 | 2 | 2 | 1 | 1 | 1 |
| | 1 | 2 | 2 | 2 | 1 | 2 | 1 | 2 | 2 |
| Total | 11 | 17 | 23 | 20 | 16 | 16 | 9 | 18 | 23 |
| Average | 1.22 | 1.89 | 2.56 | 2.22 | 1.78 | 1.78 | 1.00 | 2.00 | 2.56 |

TABLE 6

| 6 Mg Wet Add-on | | | | | | | | | |
|---|---|---|---|---|---|---|---|---|---|
| | % | | | | | | | | |
| | 3% | | | 6% | | | 9% | | |
| | Film Former | | | | | | | | |
| | PPI SIWS | PPI CO40 | Derm 79 | PPI SIWS | PPI CO40 | Derm 79 | PPI SIWS | PPI CO40 | Derm 79 |
| | Code | | | | | | | | |
| | A2(6) | D2(6) | G2(6) | B2(6) | E2(6) | H2(6) | C2(6) | F2(6) | I2(6) |
| | 3 | 2 | 1 | 1 | 1 | 2 | 2 | 2 | 2 |
| | 1 | 3 | 2 | 2 | 1 | 3 | 2 | 1 | 3 |
| | 1 | 2 | 2 | 2 | 1 | 3 | 1 | 3 | 2 |
| | 1 | 2 | 3 | 1 | 2 | 3 | 1 | 2 | 3 |
| | 2 | 2 | 1 | 2 | 1 | 2 | 1 | 2 | 3 |
| | 1 | 3 | 2 | 1 | 3 | 2 | 3 | 1 | 2 |
| | 1 | 2 | 3 | 1 | 3 | 2 | 1 | 3 | 2 |
| | 1 | 1 | 2 | 1 | 2 | 2 | 1 | 2 | 2 |
| | 2 | 1 | 2 | 1 | 2 | 2 | 1 | 2 | 2 |
| Total | 13 | 18 | 18 | 12 | 16 | 21 | 13 | 18 | 21 |
| Average | 1.44 | 2.00 | 2.00 | 1.33 | 1.78 | 2.33 | 1.44 | 2.00 | 2.33 |

As shown in Tables 3-6, PPI SI WS emulsions performed favorably, and in many embodiments provided better fragrance intensity as compared to the other samples. Five of the participants were then instructed to compare A2(3), D2(3), G2(3) and the control samples (i.e., including fragrance not in an emulsion) to choose the sample with the highest fragrance intensity. The results are shown in Table 7 below.

TABLE 7

| Control Comparison | | | | |
|---|---|---|---|---|
| Code | A2(3) | D2(3) | G2(3) | Control |
| | 1 | | | |
| | 1 | | | |
| | 1 | | | |
| | 1 | | | |
| | 1 | | | |

As shown in Table 7, the PPI SI WS emulsion samples have the highest fragrance intensity after 4 hours of dry time versus other emulsion samples and the control.

In summary, the above data show the emulsion samples of the present disclosure maintain fragrance intensity better than no emulsion (i.e., control) and further are superior in fragrance emission to all other tested samples.

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the disclosure are achieved and other advantageous results attained.

As various changes could be made in the above formulations and substrates/articles without departing from the scope of the disclosure, it is intended that all matter contained in the above description shall be interpreted as illustrative and not in a limiting sense.

What is claimed is:

1. A fragrance delivery system comprising an emulsion comprising a silicone-based polyurethane having a polymeric backbone comprising at least one lipophilic moiety and at least one hydrophilic moiety, a fragrance, and a carrier, wherein the silicone-based polyurethane and fragrance are present in a weight ratio of silicone-based polyurethane:fragrance of from about 1:3 to about 3:1.

2. The fragrance delivery system of claim 1, wherein the polymeric backbone comprises at least one dimethicone polyether.

3. The fragrance delivery system of claim 2, wherein the polymeric backbone comprises a bis-(polyethylene glycol)$_x$ dimethicone, wherein x ranges from 8 to 20.

4. The fragrance delivery system of claim 2, wherein the polymeric backbone comprises a bis-(polyethylene glycol)$_x$ dimethicone, wherein x ranges from 12 to 16.

5. The fragrance delivery system of claim 3, wherein the polymeric backbone comprises isophorone diisocyanate.

6. The fragrance delivery system of claim 1, wherein at least a portion of the emulsion is encapsulated.

7. The fragrance delivery system of claim 1, wherein the weight ratio of silicone-based polyurethane:fragrance is from about 1:2 to about 2:1.

* * * * *